US009452267B2

(12) United States Patent
Reynolds et al.

(10) Patent No.: US 9,452,267 B2
(45) Date of Patent: Sep. 27, 2016

(54) INJECTION DEVICE

(75) Inventors: David L. Reynolds, Bromont (CA);
Daniel MacDonald, Bromont (CA);
Yan Tremblay, Orford (CA); Julie Trepanier, Sherbrooke (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 87 days.

(21) Appl. No.: 13/261,424

(22) PCT Filed: Feb. 28, 2011

(86) PCT No.: PCT/CA2011/000210
§ 371 (c)(1),
(2), (4) Date: Aug. 31, 2012

(87) PCT Pub. No.: WO2011/106870
PCT Pub. Date: Sep. 9, 2011

(65) Prior Publication Data
US 2013/0018324 A1 Jan. 17, 2013

(30) Foreign Application Priority Data
Mar. 2, 2010 (CA) ...................................... 2695265

(51) Int. Cl.
*A61M 5/32* (2006.01)
*A61M 5/24* (2006.01)

(52) U.S. Cl.
CPC ......... *A61M 5/3202* (2013.01); *A61M 5/2466* (2013.01); *A61M 5/326* (2013.01); *A61M 5/3272* (2013.01); *A61M 5/3293* (2013.01); *A61M 5/3287* (2013.01); *A61M 2005/247* (2013.01); *A61M 2005/2414* (2013.01); *A61M 2005/3267* (2013.01); *A61M 2005/3289* (2013.01)

(58) Field of Classification Search
CPC ............. A61M 5/315; A61M 2005/2414; A61M 5/3272; A61M 5/3293; A61M 5/2466; A61M 2005/14506
USPC .............. 604/232, 187, 110, 218; 128/919
See application file for complete search history.

(56) References Cited

U.S. PATENT DOCUMENTS

| 1,852,658 A | * | 4/1932 | Kile ................................ 604/209 |
| 2,994,323 A | * | 8/1961 | Dann et al. .................... 604/232 |
| 3,848,593 A | * | 11/1974 | Baldwin ........................ 604/206 |
| 4,898,590 A | * | 2/1990 | Andors .................... A61M 5/24 604/198 |
| 5,403,288 A | * | 4/1995 | Stanners ........................ 604/232 |
| 5,531,683 A | * | 7/1996 | Kriesel et al. ................... 604/89 |

(Continued)

Primary Examiner — Kami A Bosworth
Assistant Examiner — Matthew A Engel
(74) Attorney, Agent, or Firm — Eric Fincham

(57) ABSTRACT

An injection device (10) comprising a housing (12), a needle hub (38) slidable within the housing (12), a needle (40) having a distal end piercing tip (42) and a proximal end piercing tip (44), the needle hub being moveable from a first position wherein the distal end piercing tip (42) is within the housing to a second position wherein the distal end piercing tip (42) extends outwardly of the housing (12), a spring (23) biasing the needle hub (38) towards the first position, and a cartridge receiving member (48) mounted within the housing (12), and a plunger rod assembly (66) for exerting pressure on the cartridge receiving member (48) to move the cartridge (26) and the needle hub (38) from the first position to the second position, the plunger rod assembly (66) and the cartridge receiving member (48) being arranged such that when the cartridge rod assembly is pushed, a rotational movement is imparted to the cartridge receiving member (48) to thereby prevent access to the cartridge after injection.

12 Claims, 3 Drawing Sheets

(56) References Cited

U.S. PATENT DOCUMENTS

| | | | | |
|---|---|---|---|---|
| 5,569,192 A * | 10/1996 | van der Wal | A61M 5/2066 | |
| | | | 604/135 | |
| 5,593,391 A * | 1/1997 | Stanners | 604/232 | |
| 5,679,111 A * | 10/1997 | Hjertman | A61M 5/20 | |
| | | | 604/135 | |
| 6,036,675 A * | 3/2000 | Thorne et al. | 604/232 | |
| 6,190,361 B1 * | 2/2001 | Gettig et al. | 604/192 | |
| 6,221,055 B1 * | 4/2001 | Shaw et al. | 604/232 | |
| 6,319,233 B1 * | 11/2001 | Jansen et al. | 604/192 | |
| 7,175,055 B2 * | 2/2007 | Hansen | A61M 5/14546 | |
| | | | 222/325 | |
| 7,297,136 B2 * | 11/2007 | Wyrick | 604/117 | |
| 2003/0105430 A1 * | 6/2003 | Lavi | A61M 5/2033 | |
| | | | 604/136 | |
| 2008/0051729 A1 * | 2/2008 | Cheng | 604/232 | |
| 2011/0034878 A1 * | 2/2011 | Radmer | A61M 5/315 | |
| | | | 604/192 | |
| 2013/0030383 A1 * | 1/2013 | Keitel | 604/232 | |
| 2013/0245604 A1 * | 9/2013 | Kouyoumjian | A61M 5/1408 | |
| | | | 604/506 | |

\* cited by examiner

INJECTION DEVICE

FIELD OF THE INVENTION

The present invention relates to a medical device and more particularly, relates to an injection device.

BACKGROUND OF THE INVENTION

Injection devices are utilized for administering a drug. There are many known injection devices, the most common of which is a syringe. Known syringes basically comprise a cylindrical tube having a needle mounted at the injection end thereof and a plunger mounted at the other end. Intermediate the needle and the plunger is the constituent to be injected.

Syringes frequently are pre-filled and while this is satisfactory for many medicaments, it is less desirable for other medicaments which must be maintained at a certain temperature. This temperature base usually requires refrigeration of the pre-filled syringe for storage purposes. As will be appreciated, a great deal of space is required for the storage of traditional syringes.

A further problem with traditional syringes is the protection of the person doing the injection. Frequently the medicament being injected can pose a risk for the medical personnel using the syringe. This problem is well known and many different devices or arrangements have been proposed in order to provide protection for the person doing the injection.

SUMMARY OF THE INVENTION

It is an object of the present invention to provide an injection device which provides protection from accidental pricking of the person doing the injection.

It is a further object of the present injection to provide an injection device which does not need to be refrigerated and which can accept a vial of a medicament and safely inject the same into the patient.

According to one aspect of the present invention, there is provided an injection device comprising a housing, an aperture in a side wall of the housing, a needle hub, a needle mounted in the needle hub, the needle having a distal end piercing tip and a proximal end piercing tip, the needle hub being slidably mounted within the housing, the needle hub being movable from a first position wherein the distal end piercing tip is within the housing to a second position wherein the distal end piercing tip extends outwardly of the housing, a spring biasing the needle hub towards the first position, a cartridge receiving member mounted within the housing, the cartridge receiving member being accessible through the aperture in the side wall of the housing, and a plunger rod assembly for exerting pressure on the cartridge receiving member to move the cartridge and the needle hub from the first position to the second position, the plunger rod assembly and the cartridge receiving member having cooperating means such that when the plunger rod assembly is pushed to cause the cartridge plunger to be pierced by the proximal end piercing tip, a rotational movement is imparted to the cartridge receiving member to thereby prevent access to the cartridge through the aperture in the side wall of the housing.

The injection device of the present invention will typically be utilized for administering a drug to a patient by qualified medical personnel. However, it will be understood that the scope of the invention is not limited to such an arrangement. In some instances, the patient may self-inject utilizing the device of the present invention. Furthermore, the device can be utilized with any animal requiring injection of the medicament.

As used herein, the distal end refers to the end through which the injection is made while the proximal end is the end closer to the hand of the person administering the injection.

The injection device may be formed of any suitable material, including glass, plastics, metallic material, combinations thereof, et cetera. It suffices to say that those knowledgeable in the art will select the materials most suitable for the manufacture of the device.

The housing functions to contain the various components of the invention and conveniently may be formed of a molded plastic or the like. The housing will also interact with the other components to assist in the motions as will be described in greater detail hereinbelow.

The needle hub is arranged to receive a needle having a distal end piercing tip and a proximal end piercing tip. The distal end piercing tip will be a typical injection piercing tip and is of a relatively small diameter as is known in the art.

The cartridge receiving member, in a preferred embodiment, is formed integrally with the needle hub and naturally is movable therewith.

The cartridge receiving member is further characterized by having a partial wall which will extend partially around the cartridge. The remainder is open to receive the cartridge through an aperture in the housing. However, upon movement of the plunger rod upwardly, the cartridge receiving member is caused to rotate such that the aperture in the housing is covered by the cartridge receiving member partial wall. Furthermore, when in the position wherein access may not be provided to the cartridge, the cartridge receiving member cannot be rotated back to its original position.

BRIEF DESCRIPTION OF THE DRAWINGS

Having thus generally described the invention, reference will be made to the accompanying drawings illustrating an embodiment thereof, in which.

DETAILED DESCRIPTION OF THE INVENTION

Figure 1:
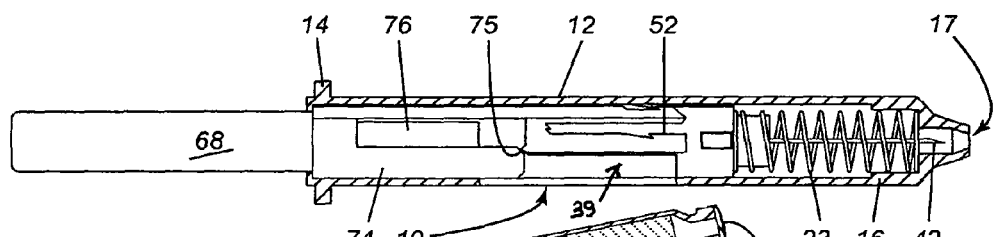
FIG. 1 is a side sectional view illustrating the device and a cartridge.

Referring to the drawings and by reference characters thereto, there is illustrated in FIGS. 1 to 10 the device of the present invention (generally designated by reference numeral 10) along with a cartridge generally designated by reference numeral 26.

Device 10 has an outer generally cylindrically shaped housing 12. A flange 14 is provided at the proximal end of housing 12 while at the distal end of housing 12 there is provided a cap 16. Cap 16 is screwthreadedly engaged with the distal end of housing 12. It will be noted that there is an aperture or opening 17 in cap 16 to provide for a needle passing therethrough. A slot 15 formed in an area adjacent flange 14 for reasons discussed hereinbelow.

Figure 11:
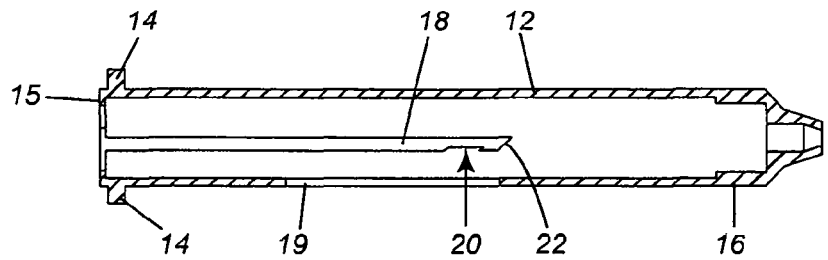
FIG. 11 is a side sectional view of the housing.
Figure 12:
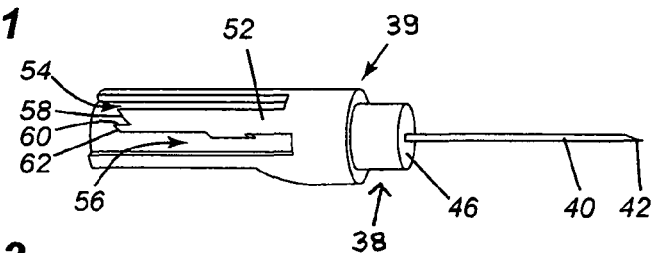
FIG. 12 is a perspective view of the needle hub and cartridge holder.
Figure 13:
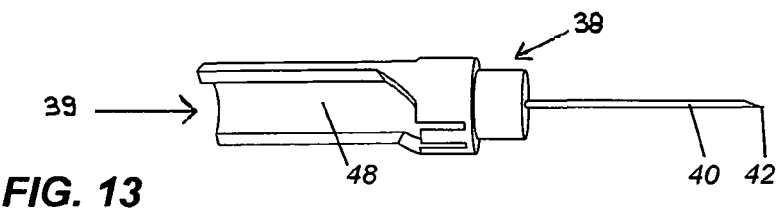
FIG. 13 is a further perspective view of the needle hub and cartridge holder.
Figure 14:
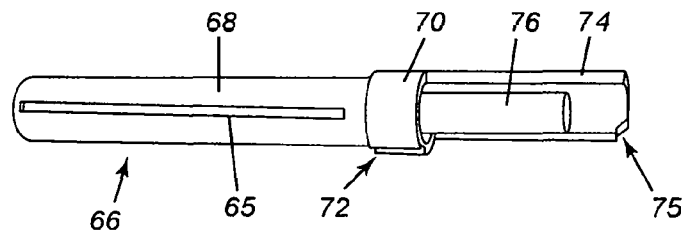
FIG. 14 is a perspective view of the plunger rod assembly.
Figure 15:
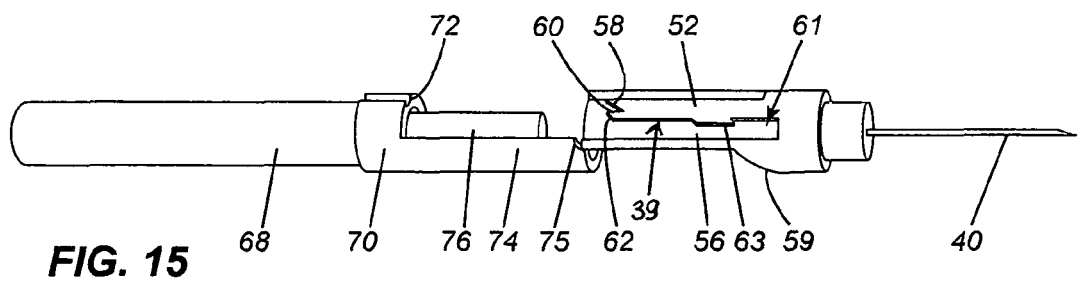
FIG. 15 is a perspective view illustrating the initial engagement of the plunger rod and needle hub.
Figure 16:
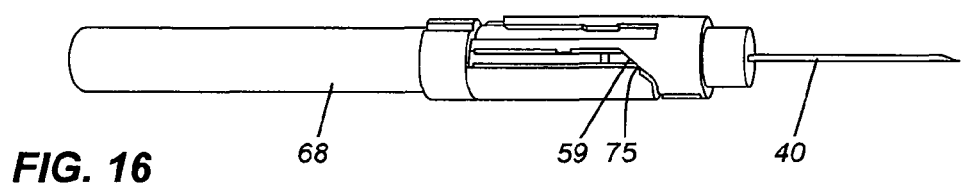
FIG. 16 is a perspective view showing the position of the needle hub and plunger rod after injection.

As may be seen in FIG. 11, there is a longitudinally extending rib 18 formed on the inner surface of housing 12. While rib 18 is shown extending a substantial length of the housing 12, it is only the upper or distal portion which is required in many embodiments. Rib 18 is provided with a recess generally designated by reference numeral 20. Rib 18 also has an angled top wall 22. An opening 19 is provided in housing 12 to permit the insertion of a cartridge as seen in FIGS. 1 to 10.

Cartridge 26 may be a standard cartridge or vial and will contain the medicament to be injected into the patient. Cartridge 26, as is conventional in the art, has a septum 28 and a cap 30 covering septum 28. A plunger 32 is mounted interiorly of the cartridge at the proximal end thereof to prevent loss of medicament 34.

A moveable needle hub 38 is mounted within housing 12 and there is provided a needle 40. Needle 40 includes a distal end piercing tip 42 for injection into the patient and a proximal piercing tip 44 which is arranged to pierce septum 28 of cartridge 26 to provide access to medicament 34.

Needle hub 38 has an upper cylindrical portion 46 and a cartridge receiving member 39 defined by a lower semi-cylindrical wall 48 depending downwardly therefrom. On the exterior of semi-cylindrical wall 48, there is formed a recess 50 which extends partially into wall 48. A raised land portion 52 is located within recess 50 to define a first channel 54 and a second channel 56. A recess 61 is formed in second channel 56 by protrusion 63. At the lower end of raised land portion 52, there is provided a first angled bottom wall 58 which meets a side wall 60 so as to form a small notch. On the opposite side, there is provided a second angled bottom wall 62. A further angled wall section 59 is provided on needle hub 38 proximate an upper portion thereof.

A plunger rod assembly generally designated by reference numeral 66 has a lower cylindrical portion 68 at the top of which there is formed a enlarged portion 70 having a slot 72 formed therein for reasons which will be discussed hereinbelow. A rib 65 is formed on the exterior of lower cylindrical portion 68 for engagement with slot 15.

Plunger rod 66 also includes an upper partial wall 74 which extends about a central pushing rod 76 which is sized to fit within vial 26 to push plunger 32. At an upper corner of upper partial will 74, there is provided a recess 75 having a hook configuration.

Figure 2:
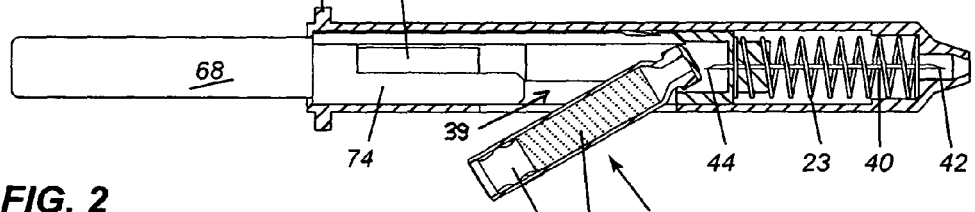
FIG. 2 is a side sectional view illustrating placement of the cartridge in the device.
Figure 3:
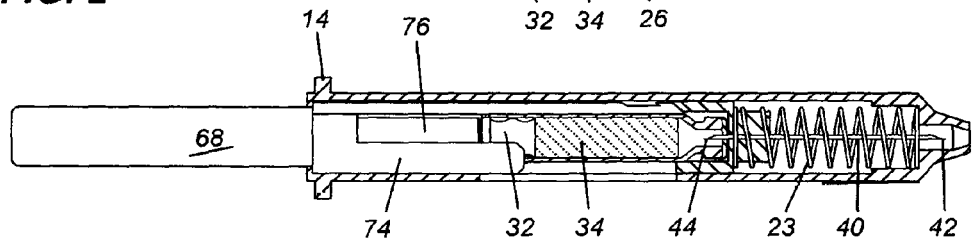
FIG. 3 is a side sectional view illustrating the cartridge in the device with piercing of the septum.
Figure 4:
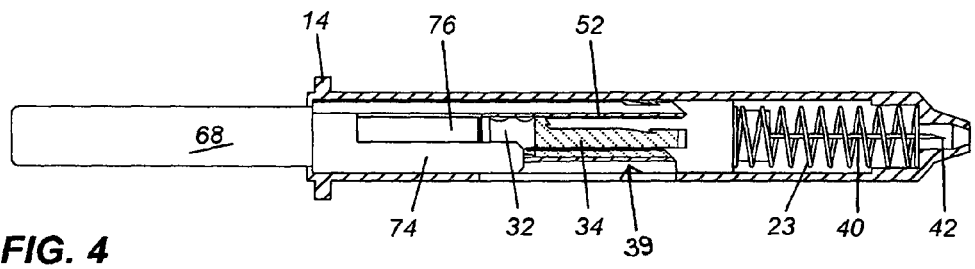
FIG. 4 is a side sectional view illustrating initial movement of the cartridge within the holder.
Figure 5:
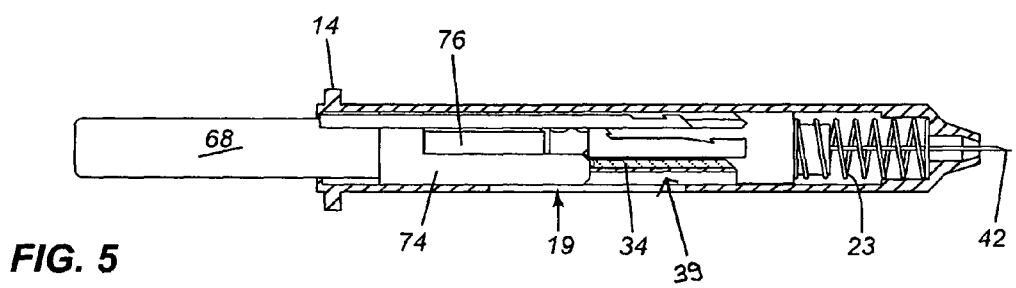
FIG. 5 is a side sectional view illustrating further movement of the cartridge and needle hub.
Figure 6:
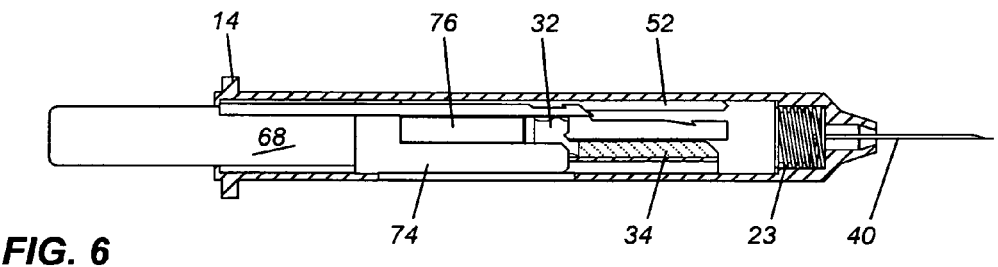
FIG. 6 is a side sectional view illustrating further movement of a plunger rod.
Figure 7:
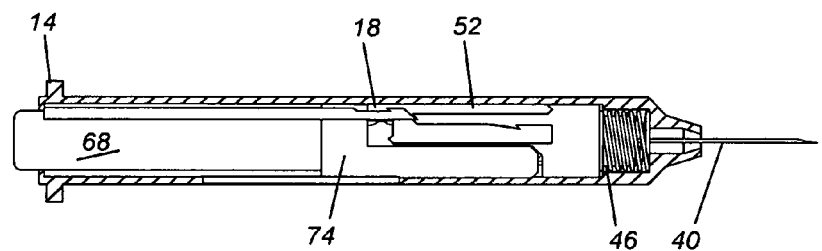
FIGS. 7 and 8 are side sectional views illustrating progression of the movement and injection of the cartridge contents.
Figure 8:
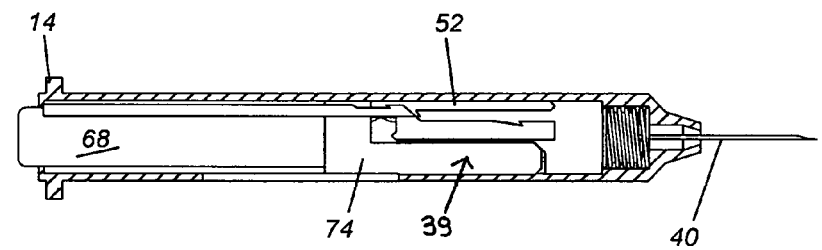
Figure 9:
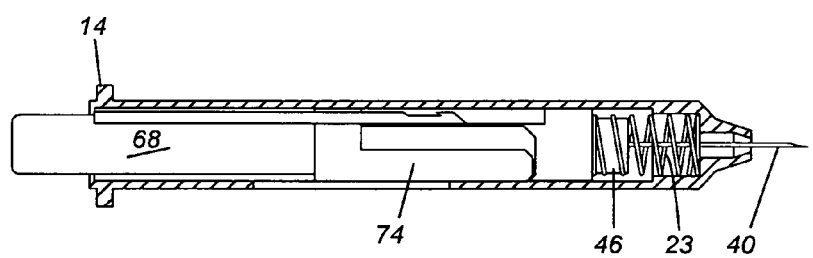
FIG. 9 is a side sectional view illustrating rearward movement of the needle hub, cartridge and cartridge holder.
Figure 10:
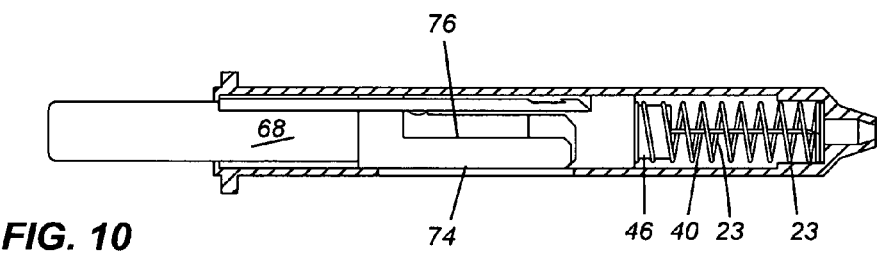
FIG. 10 is a side sectional view illustrating the device after injection and withdrawal of the needle.

Vial 26 is inserted through opening 19 in housing 12 as may be seen in FIGS. 1 and 2. If desired, it can be arranged such that vial 26 has septum 28 pierced by lower piercing end 44 upon insertion. A spring 23 extends about the upper portion of needle 40.

Initially, recess portion 75 engages end wall 62 which is tapered. The hooked nature of recess 75 ensures that the two walls remain in contact for a period of time sufficient for piercing end 44 to pierce septum 28. Continued pressure on plunger rod 66 will cause corners 75 and 71 to disengage and impart a rotational movement to needle hub 38. In turn, this will allow rib 18 to enter first channel 54. Continued pressure on plunger rod 66 will cause corner 75 to contact slanted wall 59. This causes a further rotation of needle hub 38 with respect to housing 12. This further rotation will cause the upper end of rib 18 to enter into channel 56. In so doing, pressure will be exerted until the top of rib 18 enters recess 61. The rib is then in a locked position and needle hub 38 is pushed rearwardly by spring 23. The continued engagement of the top of rib 18 within recess 61 assures that the needle cannot be exposed as it is locked in place.

We claim:

1. An injection device comprising:
   a housing (12), an aperture (19) in a side wall of said housing;
   a needle hub (38), a needle (40) mounted in said needle hub (38), said needle (40) having a distal end piercing tip (42) and a proximal end piercing tip (44); said needle hub (38) being slidably mounted within said housing (12), said needle hub (38) being movable from a first position wherein said distal end piercing tip (42) is within said housing (12) to a second position wherein said distal end piercing tip (42) extends outwardly of said housing (12);
   a spring (23) biasing said needle hub (38) towards said first position;
   a cartridge receiving member (39) mounted within said housing, said cartridge receiving member (39) being accessible through said aperture (19) in said side wall of said housing (12); and
   a plunger rod assembly (66) for exerting pressure on said cartridge receiving member (39) to move a cartridge (26) and said needle hub (38) from said first position to said second position, said plunger rod assembly (66) and said cartridge receiving member (39) having cooperating means such that when said plunger rod assembly is pushed to cause a cartridge septum to be pierced by said proximal end piercing tip, a rotational movement is imparted to said cartridge receiving member (39) causing said cartridge receiving member to rotate thereby positioning said cartridge receiving member (39) so as to block access to said cartridge through said aperture in said side wall of said housing.

2. The injection device of claim 1 wherein said cartridge receiving member (39) and said needle hub (38) are integral.

3. The injection device of claim 2 wherein said plunger rod assembly (66) has a pushing rod (76) and an upper partial wall (74) partially surrounding said pushing rod (76), said upper partial wall (74) having a length greater than said pushing rod (76).

4. The injection device of claim 3 wherein said upper partial wall (74) has an angled corner (75), said cartridge receiving member (39) having a cartridge receiving member partial wall, said cartridge receiving member partial wall having a tapered corner (62) to engage with said angled corner (75) on said upper partial wall (74) to permit pushing of said cartridge receiving member (39) upwardly.

5. The injection device of claim 4 wherein contact of said upper partial wall (74) and said cartridge receiving member partial wall causes said cartridge receiving member (39) to rotate and thereby cause said cartridge receiving member partial wall to block said aperture in said side wall of said housing to thereby prevent removal of said cartridge therefrom.

6. The injection device of claim 5 wherein said housing has a protrusion on an inner surface thereof, said cartridge receiving member (39) having first and second channels, said second channel having a recess formed therein to engage said protrusion on said inner surface of said housing to prevent further movement of said cartridge receiving member (39).

7. An injection device comprising:
 a housing (12), an aperture (19) in a side wall of said housing;
 a needle hub (38), a needle (40) mounted in said needle hub (38), said needle (40) having a distal end piercing tip (42) and a proximal end piercing tip (44); said needle hub (38) being slidably mounted within said housing (12), said needle hub (38) being movable from a first position wherein said distal end piercing tip (42) is within said housing (12) to a second position wherein said distal end piercing tip (42) extends outwardly of said housing (12);
 a spring (23) biasing said needle hub (38) towards said first position;
 a cartridge receiving member (39) mounted within said housing, said cartridge receiving member (39) being accessible through said aperture (19) in said side wall of said housing (12);
 a cartridge (26) mounted within said cartridge receiving member, said cartridge having a pierceable septum; and
 a plunger rod assembly (66) for exerting pressure on said cartridge receiving member (39) to move said cartridge (26) and said needle hub (38) from said first position to said second position, said plunger rod assembly (66) and said cartridge receiving member (39) having cooperating means such that when said plunger rod assembly is pushed to cause said cartridge septum to be pierced by said proximal end piercing tip, a rotational movement is imparted to said cartridge receiving member (39) causing said cartridge receiving member to rotate thereby blocking access to said cartridge through said aperture in said side wall of said housing.

8. The injection device of claim 7 wherein said cartridge receiving member (39) and said needle hub (38) are integral.

9. The injection device of claim 8 wherein said plunger rod assembly (66) has a pushing rod (76) and an upper partial wall (74) partially surrounding said pushing rod (76), said upper partial wall (74) having a length greater than said pushing rod (76).

10. The injection device of claim 9 wherein said upper partial wall (74) has an angled corner (75), said cartridge receiving member (39) having a cartridge receiving member partial wall, said cartridge receiving member partial wall having a tapered corner (62) to engage with said angled corner (75) on said upper partial wall (74) to permit pushing of said cartridge receiving member (39) upwardly.

11. The injection device of claim 10 wherein contact of said upper partial wall (74) and said cartridge receiving member partial wall causes said cartridge receiving member (39) to rotate and thereby cause said cartridge receiving member partial wall to block said aperture in said side wall of said housing to thereby prevent removal of said cartridge therefrom.

12. The injection device of claim 11 wherein said housing has a protrusion on an inner surface thereof, said cartridge receiving member having first and second channels, said second channel having a recess formed therein to engage said protrusion on said inner surface of said housing to prevent further movement of said cartridge receiving member.

* * * * *